United States Patent
Shaw et al.

(12) 
(10) Patent No.: US 7,740,615 B2
(45) Date of Patent: *Jun. 22, 2010

(54) IV CATHETER INTRODUCER WITH RETRACTABLE NEEDLE—CONTINUATION

(75) Inventors: Thomas J. Shaw, Little Elm, TX (US); Judy Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/148,440

(22) Filed: Apr. 18, 2008

(65) Prior Publication Data

US 2008/0215009 A1   Sep. 4, 2008

Related U.S. Application Data

(63) Continuation of application No. 11/042,941, filed on Jan. 25, 2005, now abandoned, which is a continuation of application No. 10/047,662, filed on Oct. 26, 2001, now Pat. No. 6,872,193.

(51) Int. Cl.
*A61M 5/178* (2006.01)

(52) U.S. Cl. .............. 604/168.01; 604/110; 604/164.01

(58) Field of Classification Search ................ 604/110, 604/164.01, 164.07, 164.08, 164.12, 192, 604/900, 158, 164.02, 164.04, 164.06, 164.09, 604/164.11, 167.01, 167.02, 198
See application file for complete search history.

(56) References Cited

U.S. PATENT DOCUMENTS

| | | | |
|---|---|---|---|
| 4,747,831 A | 5/1988 | Kulli | |
| 4,828,548 A | 5/1989 | Walter | |
| 5,129,884 A | 7/1992 | Dysarz | |
| 5,501,675 A | 3/1996 | Erskine | |
| 5,573,510 A | 11/1996 | Isaacson | |
| 5,746,215 A | 5/1998 | Manjarrez | |
| 5,817,058 A * | 10/1998 | Shaw | 604/110 |
| 5,989,220 A | 11/1999 | Shaw et al. | |
| 6,056,726 A | 5/2000 | Isaacson | |
| 6,083,202 A | 7/2000 | Smith | |
| 6,090,078 A | 7/2000 | Erskine | |
| 6,096,005 A * | 8/2000 | Botich et al. | 604/110 |
| 6,872,193 B2 * | 3/2005 | Shaw et al. | 604/164.07 |

\* cited by examiner

*Primary Examiner*—Theodore J Stigell
(74) *Attorney, Agent, or Firm*—Locke Lord Bissell & Liddell, LLP

(57) ABSTRACT

An IV catheter introducer having a retractable needle holder and a tubular plunger that are held by a detent structure in a preferred positional relationship prior to and during insertion of the catheter. Following insertion, the plunger is pushed past the detent structure, permitting a compressed spring to force the needle holder upwardly into the plunger. A vented end cap in the plunger permits rapid venting of air displaced during retraction of the needle holder. The needle holder includes a flash chamber that is easily viewable through a clear plastic housing. Wings are provided on the housing to facilitate one-handed operation of the device. A method for assembling the subject catheter introducer is also disclosed.

3 Claims, 3 Drawing Sheets

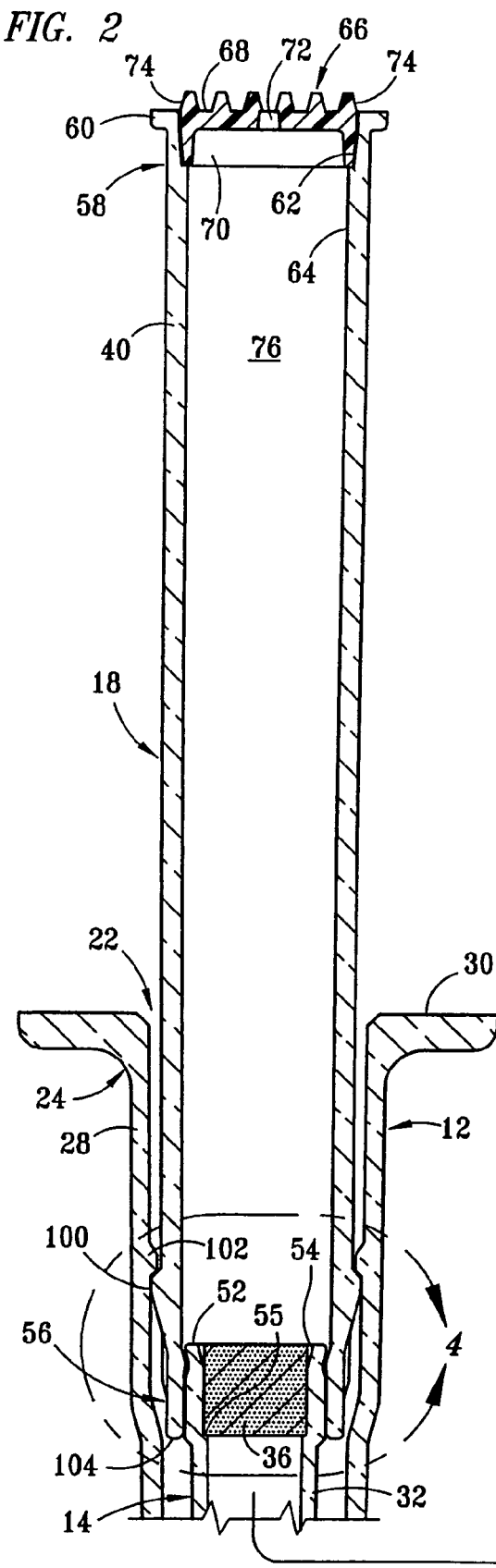
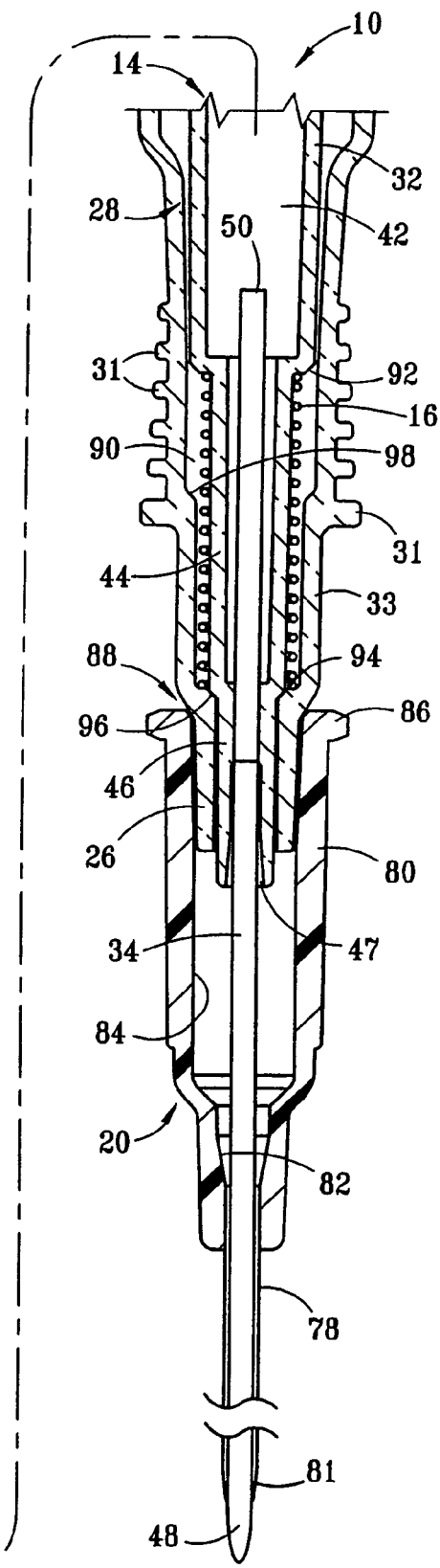
FIG. 2

IV CATHETER INTRODUCER WITH RETRACTABLE NEEDLE—CONTINUATION

CROSS-REFERENCE TO RELATED APPLICATIONS

This application is a continuation of U.S. application Ser. No. 11/042,941, filed Jan. 25, 2005, now abandoned, which is a continuation of U.S. application Ser. No. 10/047,662, filed Oct. 26, 2001, now issued as U.S. Pat. No. 6,872,193.

BACKGROUND OF THE INVENTION

1. Field of the Invention

The invention is a medical device used to insert a catheter into a patient's body, especially for the intravenous delivery of a fluid. More particularly, the invention is a catheter introducer having a retractable needle that prevents reuse and avoids needle stick injuries to medical personnel and others.

2. Description of Related Art

Catheter insertion devices are well known. When a catheter is inserted into a patient for the intravenous delivery of a fluid, a disposable needle passing through the catheter is utilized to puncture a vein to permit entry of the catheter. The needle is then withdrawn, leaving the catheter in place for connection to an IV bag or bottle, or to be capped for later use.

In recent years, because of the prevalence of blood-borne pathogens such as HIV and hepatitis, there has been an increasing need for catheter introducers that prevent accidental needle stick injuries to medical personnel and to other employees who handle trash, laundry or other refuse containing used needles. As a result, new products have been designed that incorporate special needle covers or mechanisms for retracting the needle following use. Such devices are disclosed, for example, in U.S. Pat. Nos. 4,747,831; 4,828,548; 5,129,884; 5,501,675; 5,817,058 and 5,989,220. Many of the prior art devices contain numerous complicated parts that substantially increase manufacturing costs and interfere with the user's ability to feel when the needle is properly inserted into the patient. Other devices require two-handed operation or are prone to premature needle retraction during shipment, storage and handling.

An IV catheter introducer is therefore needed that can be manufactured economically and reliably at high speed, that will not retract the needle prematurely, that can be operated with one hand, and that will fully protect the user and others from accidental sticks and exposure to blood-borne pathogens. These and other advantages are provided by the invention disclosed below.

SUMMARY OF THE INVENTION

A single use IV catheter introducer is disclosed that provides significant advantages over prior art devices, even those comprising retractable needles. Principal structural improvements include a reliable detent structure that holds the needle holder and plunger in proper positional alignment prior to needle retraction following insertion of the catheter; a plunger end cap that vents air displaced from inside the plunger bore during needle retraction; and a transparent viewing area that permits the user to view the flash chamber of the needle holder more easily through the clear plastic housing. Other improvements include barrel wings that facilitate one-handed operation and prevent the catheter introducer from rolling when placed on a surface, a needle holder opening that is tapered to permit easy insertion of the flash chamber plug during manufacture, and a needle holder configuration that prevents the blunt needle end from being occluded during manufacture and makes the flow of blood into the flash chamber more visible.

The IV catheter introducers of the invention have few parts, can be manufactured reliably at high speed, significantly reduce the likelihood of premature needle retraction during storage and handling, are easily useable in one hand, and will protect medical and other ancillary personnel from accidental needle sticks and the possibility of resultant infection by blood-borne pathogens. Use of the present invention also affords significant economic benefits to health care providers and insurers through reduced testing and follow-up costs.

BRIEF DESCRIPTION OF THE DRAWINGS

The apparatus of the invention is further described and explained in relation to the following figures of the drawing wherein:

FIG. 2 is an enlarged, cross-sectional elevation view taken along line 2-2 of FIG. 1;

FIG. 4 is an enlarged detail view taken from FIG. 2, and depicts the detent structure holding the landed front opening of the plunger tube in the desired position relative to the retractable needle holder prior to retraction;

FIG. 5 is an enlarged plan view of the vented plunger end cap; and

FIG. 6 is a cross-sectional elevation view taken along line 6-6 of FIG. 5.

Like reference numerals are used to describe like parts in all figures of the drawings.

DETAILED DESCRIPTION OF THE PREFERRED EMBODIMENT

Figure 1:
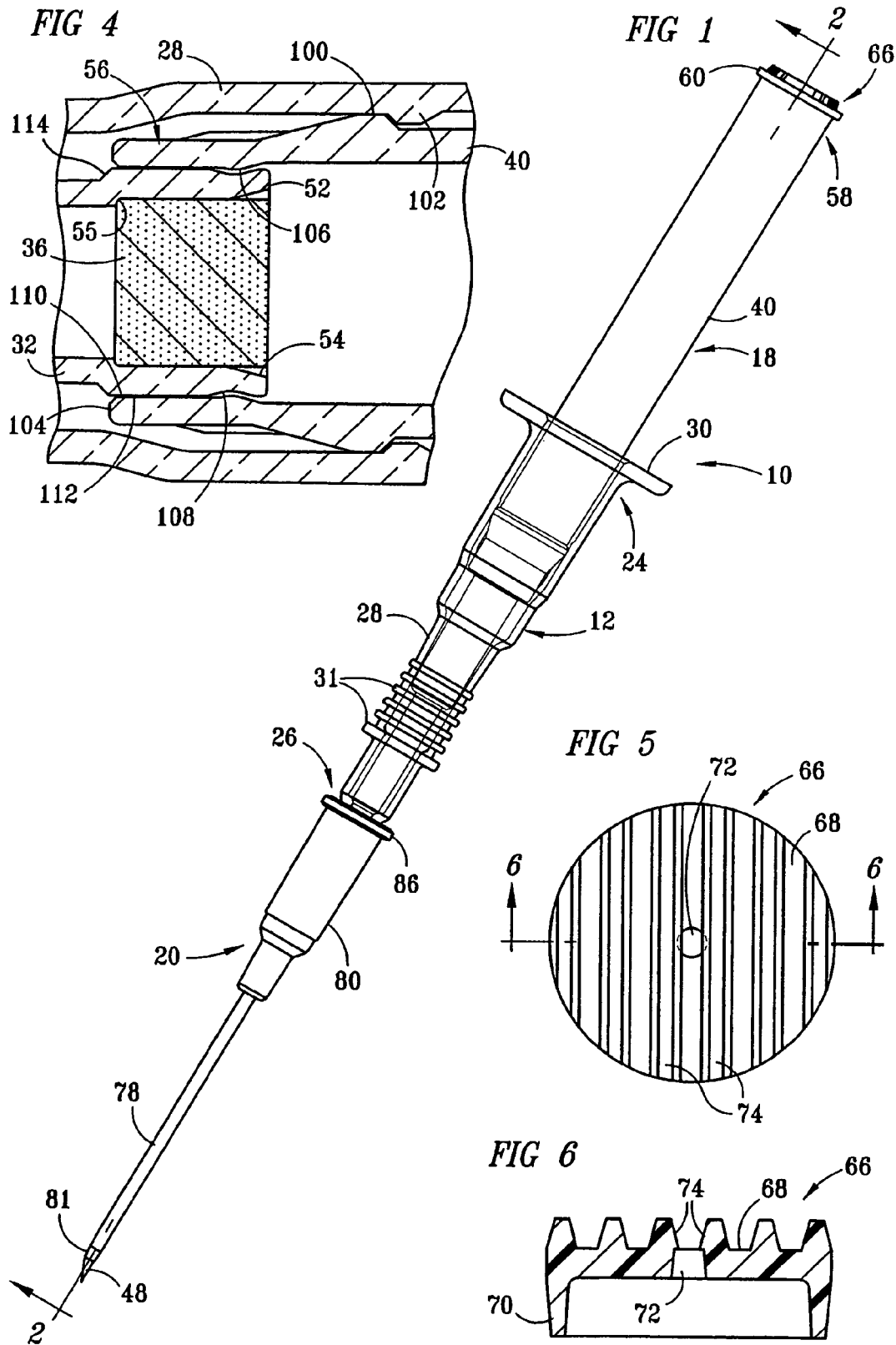
FIG. 1 is a simplified perspective view of the IV catheter introducer of the invention with the catheter needle ready for use.

Referring to FIGS. 1-2, IV catheter introducer 10 preferably comprises tubular plastic housing 12, needle holder assembly 14, retraction mechanism 16, plunger assembly 18 and IV catheter 20. Plastic housing 12 has an internal bore 22 that narrows progressively between open end 24 and reduced diameter tip 26, except for a short distance below inwardly projecting annular ring 102, as described below. Plastic housing 12 is preferably injection molded from a substantially transparent polymeric resin such as polycarbonate to permit easy viewing through sidewall 28. The outside diameter of housing 12 generally follows the tapered narrowing of internal bore 22, so that sidewall 28 has a substantially constant thickness except where it flares outwardly to form laterally extending wings 30 and to provide a longitudinally spaced series of annular ridges 31 nearer to tip 26 to create a textured gripping area for the fingers of the user.

Needle holder assembly 14 is retractably mounted within the lower portion of housing 12 and preferably comprises a tapered, elongate tubular body 32, needle 34 and porous plug 36. Body 32 of needle holder assembly 14 is preferably injection molded from a substantially transparent polymeric resin such as polycarbonate and comprises a tapering sidewall of substantially constant thickness that further defines flash chamber 42, spring guide section 44 and needle support section 46, each of which has a progressively smaller diameter. Tubular body 32 of needle holder assembly 14 is desirably shaped so as to permit needle holder assembly 14 to be inserted into sliding engagement with housing 12 during assembly, as described in greater detail below. The upper end portion of tubular body 32 is adapted to releasably engage lower end 56 of plunger assembly 18 as described below in relation to FIG. 4. As viewed in FIG. 2, retraction mechanism 16, which is preferably a spring, is confined within annular space 90 between housing 12 and spring guide section 44 of tubular body 32, and is held in compression between downwardly facing shoulder 92 of tubular body 32 and upwardly facing shoulder 94 of housing 12. Although this embodiment uses a compressed spring that exerts a retraction force by expanding, other similarly effective means such as an extension spring can likewise be used to retract the needle.

Needle 34 is hollow and has a beveled end 48, which is inserted into a patient's vein during use, and a blunt end 50 that extends into flash chamber 42. A longitudinally extending bore provides fluid communication through needle 34 between beveled end 48 and blunt end 50. Needle 34 is preferably insert molded into needle support section 46 of tubular body 32 to create an insert molded needle. However, needle 34 can be glued or sonically welded into body 32 if desired. A tapered needle insertion opening 47 is desirably provided at the lower end of needle support section 46 if needle 34 is to be inserted after molding needle support section 46. By using a needle 34 that is long enough to extend into flash chamber 42, the bore of needle 34 will not become occluded during insert molding. Also, because a minor amount of blood flows upwardly through needle 34 into flash chamber 42 whenever needle 34 is introduced into the vein of a patient, making blunt end 50 visible in flash chamber 42 permits the user to view blood as soon as it enters flash chamber 42, confirming to the user that needle 34 is properly positioned inside the vein.

At the top of flash chamber 42 of needle holder assembly 14, end 52 of tubular body 32 is blocked with porous plug 36 that frictionally engages the walls of annular recess 55 in body 32. The insertion of porous plug 36 into tubular body 32 is preferably made easier by tapered inside wall 54 adjacent to end 52. Porous plug 36 is preferably made of any suitable porous material that will allow air to be displaced out of needle 34 and flash chamber 42 by blood rising through needle 34 following insertion into a vein, but will prevent any such minor amount of blood from exiting flash chamber 42. A significant advantage of IV catheter introducer 10 disclosed herein is that flash chamber 42 is visible through only two layers of clear plastic: the transparent wall of tubular body 32 around flash chamber 42; and the transparent wall of housing 12. With many devices disclosed in the prior art, the user must peer through three or more plastic layers to view the flash chamber, making it more difficult to observe when blood begins entering the chamber.

Plunger assembly 18 preferably comprises a polymeric plunger tube 40 having a substantially cylindrical sidewall with a lower end portion 56 that is proximal to end 52 of tubular body 32 of needle holder assembly 14, and an upper end portion 58 that projects longitudinally outward from open end 24 of housing 12. Plunger tube 40 is preferably injection molded from a polymeric resin, and most preferably, from a substantially transparent polymer such as polycarbonate. Lower end portion 56 of plunger assembly 18 releasably engages tubular body 32 of needle holder assembly 14 and cooperates with needle holder assembly 14 to form the detent structure of the invention as described in greater detail below in relation to FIG. 4. Upper end portion 58 of plunger tube 40 preferably comprises a small, radially extending annular flange 60 surrounding a tapered annular recess 62 in surface 64 that receives and frictionally engages end cap 66, which is further described and explained in relation to FIGS. 5 and 6.

With IV catheter introducer 10 prepared for use, upper end 58 of plunger assembly 18 desirably extends from about 1.5 to about 3 inches from housing 12 so that upper end 58 can be nestled against the palm of the hand while the user's fingers grip wings 30 or annular ridges 31 of housing 12 to facilitate one-handed operation. Pulling back on housing 12 with the fingers triggers retraction of needle holder assembly 14, as discussed below in relation to FIG. 3.

Referring to FIGS. 5 and 6, end cap 66 is preferably molded from a polymeric resin and, most preferably, from a resin that is pigmented in a color chosen to correspond to the gauge of needle 34, shown in FIGS. 1-2, to assist users in readily differentiating among IV catheter introducers 10 having different sized needles. End cap 66 preferably further comprises a substantially continuous, circular end wall 68 connected to a longitudinally extending annular skirt 70 that is inwardly tapered to provide contacting frictional engagement with annular recess 62 of plunger tube 40 as previously described. It should be understood that there are many ways of engaging end cap 66 into upper end portion 58 of plunger tube 40. End cap 66 may be glued, snapped-on, sonically welded, dual shot molded or engaged by any other similarly effective means. Dual shot molding refers to any molding process that allows different materials or different colored materials to be molded concurrently. Vent hole 72 is preferably centrally disposed in end wall 68 and is desirably surrounded by surface relief features such as a plurality of outwardly extending molded ribs 74 that extend across surface 68. Ribs 74 are preferably of sufficient number, spacing and height that vent hole 72 is not blocked by the hand of the user, even when part of the hand is placed over end cap 66 during operation of IV catheter introducer 10. Vent hole 72 is preferably large enough to rapidly vent the volume of air displaced from retraction cavity 76 when needle holder assembly 14 is retracted into plunger tube 40 following insertion of the catheter.

Referring again to FIGS. 1-2, IV catheter 20 preferably includes a flexible rubber or plastic cannula 78 and a hub 80 having a needle channel 82 and a tubular section 84 with an annular flange 86 defining an opening 88 having a diameter such that opening 88 will receive and frictionally engage tip 26 of housing 12. At the end of cannula 78 is an inwardly tapered end 81 that provides an interference fit near beveled end 48 of needle 34. During the attachment of hub 80 to tip 26, needle 34 is inserted through flexible cannula 78 and inwardly tapered end 81, with beveled end 48 extending slightly beyond the inwardly tapered end 81. The inside diameter of cannula 78 is preferably slightly greater than the outside diameter of needle 34 to permit easy retraction of needle 34 through cannula 78 following insertion. Hub 80 is preferably also adapted for easy connection to a convention IV tubing connector following retraction of needle 34 and removal of tip 26 from tubular section 84 of hub 80.

Referring to FIG. 2, IV catheter introducer 10 of the invention is preferably assembled by dropping retraction spring 16 through opening 22 into housing 12. Retraction spring 16, which is a coil spring biased against compression, preferably has a diameter that causes it to seat just above inclined annular shoulder 94 inside housing 12, where it is supported in substantially vertical alignment by section 33 of sidewall 28. Pre-manufactured needle holder assembly 14 is then inserted downwardly through open end 22 of housing 12, with beveled end 48 of needle 34 passing downwardly through retraction spring 16 and tip 26 of housing 12, until inclined annular shoulder 96 of tubular body 32 abuts against shoulder 94 of housing 12. Alternatively, spring 16 can be placed over needle holder assembly 14 prior to insertion of needle holder assembly 14 into housing 12. Also, if desired, needle 34 can be glued or sonically welded into needle holder assembly 14 after needle holder assembly 14 is inserted into housing 12. Inclined annular shoulder 92 of tubular body 32 preferably will not contact inclined annular shoulder 98, to permit shoulder 96 to seat properly against shoulder 94.

Referring to FIGS. 2 and 4, lower end portion 56 of premanufactured plunger assembly 18 is next introduced into housing 12 through opening 22. As plunger tube 40 travels downwardly into housing 12, nose 104 of plunger tube 40 reaches and slides over end 52 of tubular body 32 of needle holder assembly 14. When nose 104 reaches end 52, radially extending annular boss 100 on plunger tube 40 is still disposed above inwardly projecting annular ring 102 of housing 12, and the inside diameter of plunger tube 40 at nose 104 is sufficiently greater than the outside diameter of end 52 to permit lower end portion 56 of plunger tube 40 to slidably engage the portion of tubular body 32 that is adjacent to end 52. As plunger assembly 18 is inserted farther into housing 12, annular boss 100 engages and overrides annular ring 102. Annular ring 102 then resists rearward movement of plunger tube assembly 18 and combined needle holder assembly 14 once they are installed in the housing with the needle extended for use. If there is an attempt to withdraw the plunger tube assembly 18 from housing 12, the shoulder of annular boss 100 will contact the shoulder of annular ring 102 and prevent the withdrawal unless there is an exertion of substantial force. However, it should be understood that annular ring 102 is desirably sufficiently small to allow for the withdrawal of a molding tool during the manufacturing process. Referring to FIG. 4, a detail view taken from FIG. 2, plunger tube 40 continues to slide downwardly over tubular body 32 of the needle holder assembly until inwardly facing annular boss 106 on the inside surface of lower end portion 56 reaches and snaps into engagement with cooperatively sized and aligned, outwardly facing annular recess 108 of tubular body 32. Referring to FIGS. 2 and 4, the configuration and dimensions of annular boss 106 and annular recess 108 cause boss 106 to be biased radially inward into annular recess 108.

It should be understood that boss 106 on the inside of plunger tube 40, is not required to be circumferentially coextensive with annular recess 108 of tubular body 32. Thus, for example, boss 106 can instead comprise a circumferentially spaced array of discrete, inwardly extending bumps that are biased into engagement with recess 108. It is preferred, however, that recess 108 extend completely around tubular body 32 so that the slidable engagement between plunger tube 40 and tubular body 32 does not require a specific rotational alignment between the two parts. The configuration and dimensions of boss 106 and recess 108 are preferably such that the force required to slidably disengage boss 106 from recess 108 by forcing plunger tube 40 farther down into housing 12 is greater than the biasing force being exerted against needle holder assembly 14 by compressed retraction spring 16 and by the additional force that is exerted upwardly on the needle 34 during catheter insertion procedures. IV catheter 20 can be assembled to tip 26 of housing 12 prior to the insertion of needle holder assembly 14 and plunger assembly 18 into housing 12. Alternatively, plunger assembly 18 and needle holder assembly 14 (sometimes referred to as a needle support assembly) can also be assembled to each other prior to insertion into housing 12. The frictional engagement between boss 106 and recess 108 when they are cooperatively engaged is preferably sufficient to permit needle holder assembly 14 and plunger assembly 18 to be inserted together into housing 12.

Beveled needle end 48 and a portion of cannula 78 are desirably inserted into a patient's vein while grasping annular ridges 31 of housing 12 with the thumb and fingers. Following insertion of the catheter into a patient, needle holder assembly 14 is retracted by grasping wings 30 or annular ridges 31 with one's fingers, or thumb and fingers, and then using the palm or heel of the hand against end cap 66 to force plunger tube 40 farther down into housing 12. When this occurs, the frictional engagement between boss 106 and recess 108, as seen in FIG. 4, is over-pressured, causing boss 106 to ride up onto surface 112 of tubular body 32. Continued downward movement of plunger tube 40 relative to tubular body 32, which is firmly seated against housing 12, causes boss 106 to drop off inclined shoulder 114 of tubular body 32. When this occurs, there is no remaining significant frictional force being exerted against compressed retraction spring 16, and spring 16 rapidly expands, causing needle holder assembly 14 to be propelled upwardly into retraction cavity 76, simultaneously withdrawing needle 34 at least to a position where beveled end 48 is withdrawn into housing 12.

Figure 3:
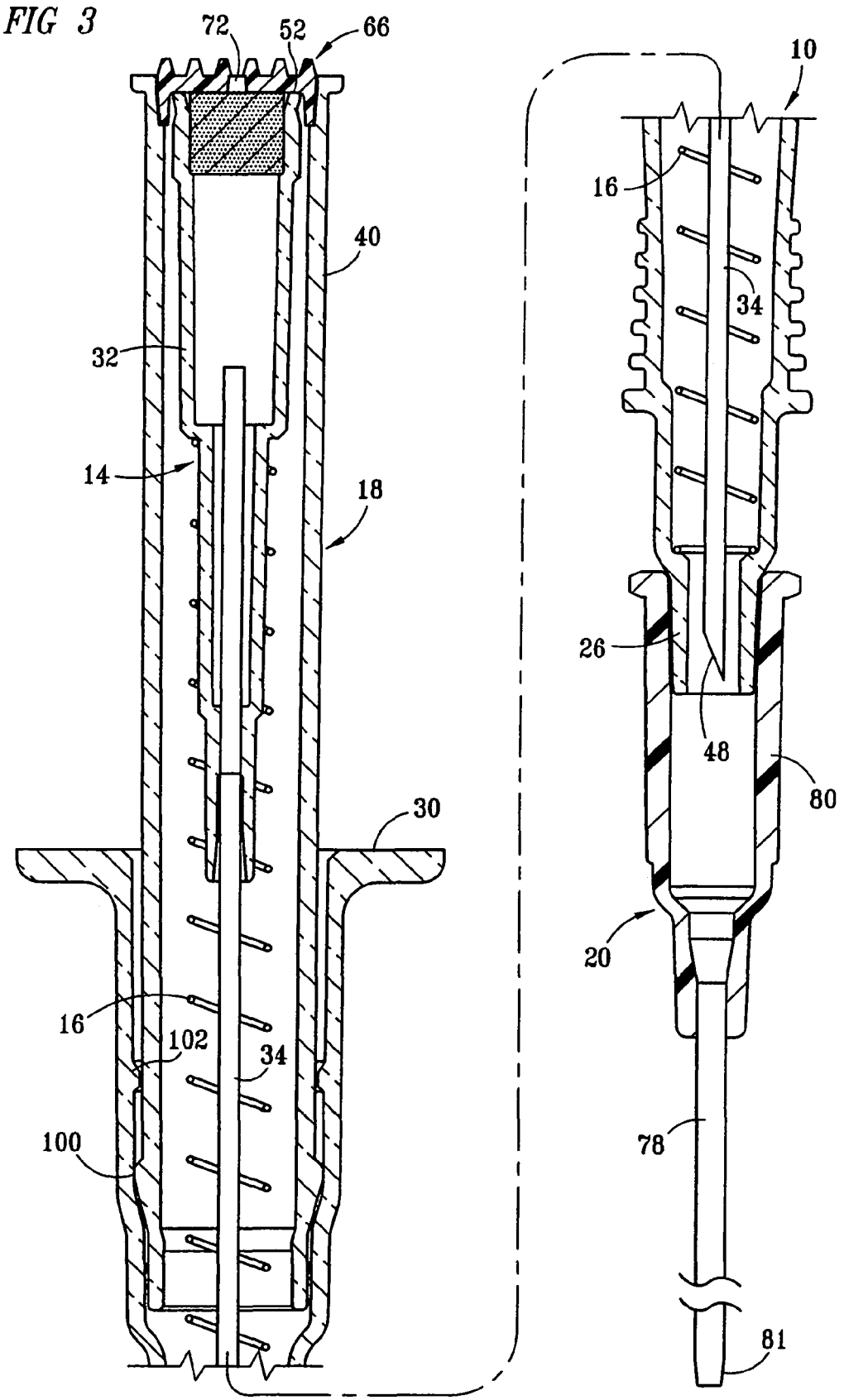
FIG. 3 is a view as in FIG. 2, but with the needle retracted following use.

Referring to FIG. 3, retraction spring 16 is fully expanded and top end 52 of needle holder assembly 14 is at least partially withdrawn into retraction cavity 76. Air previously present in retraction cavity 76 of plunger tube 40 has been vented through vent hole 72 as needle holder assembly 14 moved upwardly within the cavity in response to expansion by retraction spring 16. Top end 52 of needle holder assembly 14 has moved upward within retraction cavity 76 sufficiently that beveled end 48 of needle 34 is withdrawn into housing 12. When needle 34 is in the position shown in FIG. 3, tip 26 of housing 12 can be safely detached from IV hub 80.

The improved IV catheter introducer of the invention is well suited for automated manufacture and assembly. Aside from the catheter, needle and spring, only a housing, retractable needle holder and a capped, vented plunger tube are needed. Although housing 12 can be made in a straight configuration with a straight internal wall, it is preferably made with a stepped configuration that, with the exception of the lower shoulder of annular ring 102, tapers inwardly from top to bottom. This taper makes it easy to withdraw a core mandrel used in the molding process. Although not illustrated in the drawings, it should be understood that beveled end 48 of needle 34 is preferably protected during the manufacturing process, shipping and storage by a tubular cover that slides upwardly over the outside of cannula 78, preventing the needle from being damaged.

An important aspect of the subject IV catheter introducer is the fact that the operator can conveniently operate the retractable introducer structure with one hand. One handed operation is possible because the plunger tube desirably extends about 1.5 to about 3 inches past where the wings of the housing are located. This allows force to be applied against the plunger tube by the fleshy part of the palm while using the fingers behind the wings or the annular ridges of the housing to resist the force and smoothly initiate retraction. The other hand remains free to grasp the hub of the catheter. Timing for freeing the hub from the introducer device and attaching an IV tube to the hub is under complete control of the operator. In one motion, the hub of the catheter can be separated from the insertion device, which can then be safely set aside while the connection is then made to the IV tube or other device that is to be connected to the patient. The catheter introducer can be safely set aside without concern onto a bed or tray, because the needle has already been safely retracted before the catheter assembly is disconnected from the housing. When the fingers pull back on the wings or annular ridges of the housing to trigger retraction, the operator can both hear and see that the needle is safely retracted and immediately disengage and safely set aside the device to free his hand for use in making the necessary IV connection before loss of fluid from the patient occurs.

The IV catheter introducer of the invention does not have to resist as much force imposed by the needle on the retraction parts as does a conventional syringe that is required to puncture a rubber seal commonly used on vials. Consequently, the retractable parts need only be able to resist the force encountered during normal clinical use without retracting. With the apparatus disclosed herein, dimensional tolerances and differential thermal expansion rates are less critical than with devices where the only frictional engagement is provided by surface-to-surface contact between smooth facing surfaces.

The IV catheter introducer disclosed herein is less likely to retract the needle prematurely than prior art devices, even when subjected to rough handling and widely varying temperatures and humidity during shipment and storage prior to use. The invention has a simple, streamlined shape and a retraction spring that is simpler to operate and more reliable than others previously used. The device can be operated with one hand in any rotational position where the wings are accessible because it has no external latches that require placing the device in a particular orientation. Further, the wings prevent the catheter introducer from rolling when placed on an oblique surface. With the device held in the hand, the retraction force is applied linearly along the main longitudinal axis. A very short stroke movement is sufficient to trigger retraction. Successful retraction is noted both visually and audibly because the operator can easily see the retracted parts in the housing and retraction creates an unobtrusive noise.

Other alterations and modifications of the preferred embodiment described above will become apparent to those of ordinary skill in the art upon reading this disclosure, and it is intended that the scope of the invention disclosed herein be limited only by the broadest interpretation of the appended claims to which the inventor is legally entitled.

The invention claimed is:

1. An IV catheter introducer comprising:
    a tubular housing made of substantially transparent polymeric resin having an open end and a plurality of laterally extending wings at the open end;
    a catheter attached by frictional engagement to the tubular housing;
    a needle holder assembly having a tubular body made of substantially transparent polymeric resin that is slidably engaged inside the tubular housing and that further comprises a flash chamber, an end of the needle holder assembly blocked with a porous plug, wherein the needle holder assembly is movable between a first position and second position;
    a needle attached to the needle holder assembly, the needle having a beveled end and a blunt end that extends into the flash chamber;
    a retraction mechanism seated in an annular space between the tubular housing and the needle holder assembly;
    a plunger assembly having a plunger tube releasably engaged with the tubular body inside the tubular housing, the plunger tube being depressible inside the tubular housing by pressure applied to the plunger tube by a palm of a user, the depression of the plunger tube causing disengagement between the plunger tube and tubular body thereby allowing the retraction mechanism to move the needle holder assembly from the first position to the second position; and
    wherein in the first position, the tubular body is engaged with the plunger tube so that the flash chamber is positioned completely within the tubular housing and the flash chamber is visible through only two layers of substantially transparent polymeric resin, and in the second position, the tubular body is positioned within the plunger tube so that the beveled end is positioned within the tubular housing.

2. The IV catheter introducer of claim 1 wherein the substantially transparent polymeric resin is polycarbonate.

3. The IV catheter introducer of claim 1 wherein the retraction mechanism comprises a spring.

* * * * *